United States Patent
Shin et al.

(10) Patent No.: US 7,994,213 B2
(45) Date of Patent: Aug. 9, 2011

(54) COATING AGENT FOR DRUG RELEASING STENT, PREPARATION METHOD THEREOF AND DRUG RELEASING STENT COATED THEREWITH

(75) Inventors: Kyong-Min Shin, Seoul (KR); Dong-ki Lee, Seongnam-si (KR); Don-haeng Lee, Seoul (KR); Kun Na, Bucheon-si (KR); Eun-ae Jo, Seoul (KR)

(73) Assignees: Taewoong Medical Co., Ltd., Gyeonggi-do (KR); Kyong-Min Shin, Seoul (KR)

( * ) Notice: Subject to any disclaimer, the term of this patent is extended or adjusted under 35 U.S.C. 154(b) by 545 days.

(21) Appl. No.: 12/154,863

(22) Filed: May 28, 2008

(65) Prior Publication Data

US 2009/0286864 A1    Nov. 19, 2009

(30) Foreign Application Priority Data

Jun. 1, 2007    (KR) .......................... 10-2007-0053887

(51) Int. Cl.
| | |
|---|---|
| A61K 31/337 | (2006.01) |
| A61K 9/14 | (2006.01) |
| A61K 47/48 | (2006.01) |
| A61K 31/56 | (2006.01) |
| A61K 31/131 | (2006.01) |
| A01N 43/02 | (2006.01) |
| A61F 2/82 | (2006.01) |
| A61F 13/00 | (2006.01) |

(52) U.S. Cl. ........ 514/449; 424/422; 424/423; 424/489; 514/772.1; 514/169; 514/171; 514/673

(58) Field of Classification Search .................... 514/449
See application file for complete search history.

(56) References Cited

U.S. PATENT DOCUMENTS

| 3,189,578 A * | 6/1965 | Kuemmerer .................... 528/49 |
| 7,056,532 B1 * | 6/2006 | Kabanov et al. ............... 424/486 |
| 2002/0165179 A1* | 11/2002 | Baker, Jr. ......................... 514/44 |
| 2003/0040790 A1* | 2/2003 | Furst ............................ 623/1.11 |

OTHER PUBLICATIONS

Kwangmeyung Kim, et al., Cell-Permeable and Biocompatible Polymeric Nanoparticles for Apoptosis Imaging, J. Am. Chem. Soc. 128, 3490-3491 (2006), 2 pages.*
Merriam Webster, Desoxycholate—Medical Definition and More from Merriam-Webster [Downloaded Jan. 2, 2011] [Retrieved from internet <URL: http://www.merriam-webster.com/medical/desoxycholate>], 3 pages.*
New Zealand Pharmaceuticals, Sodium Deoxycholate [Retrieved Jan. 2, 2011] [Downloaded from internet <URL: http://www.nzp.co.nz/products.php?cid+2&pid=251>], 1 page.*
Medicinenet, Pacliltaxel—Injection (Taxol) side effects, medical uses, and drug interactions [Downloaed Jan. 2, 2011] [Retrieved from internet <URL: http://www.medicinenet.com/paclitaxel-injection/article.html.], 2 pages.*

* cited by examiner

*Primary Examiner* — Ernst V Arnold
*Assistant Examiner* — Miriam A Levin
(74) *Attorney, Agent, or Firm* — IP & T Group LLP

(57) ABSTRACT

Disclosed are a coating agent for drug releasing stents, a method for preparing the same and a drug releasing stent coated therewith. The coating agent for drug releasing stents comprises nanoparticles with a biologically active material entrapped therein, wherein the particles are formed of a polyethyleneimine (PEI)-deoxycholic acid (DOCA) polymer (PDo) in which 1~8 moles of DOCA are grafted per mole of PEI.

2 Claims, 2 Drawing Sheets

COATING AGENT FOR DRUG RELEASING STENT, PREPARATION METHOD THEREOF AND DRUG RELEASING STENT COATED THEREWITH

This application claims priority to Korean Patent Application Number 10-2007-0053887 filed in the Republic of Korea on Jun. 1, 2007, the entire disclosure of which is incorporated herein by reference.

BACKGROUND OF THE INVENTION

1. Field of the Invention

The present invention relates to a coating agent for drug releasing stents, a method for preparing the same and a drug releasing stent coated therewith. More particularly, the present invention relates to a coating agent for use in stents capable of controlled drug release, a preparation method thereof, and a drug releasing stent coated therewith.

2. Description of the Related Art

A stent is a tubular prosthesis or support, which is now widely used to hold open a natural conduit, such as a lumen, vessel, etc., to allow access for surgery or related invasive chemical treatment and to prevent the stenosis of the conduit. Furthermore, the insertion and expansion of a stent within the esophagus, the respiratory organs, the vessels, the urinary organs, and other lumens which are difficult to access has proven an influential therapy for diseases occurring therein.

A colo-rectal stent, developed in the late 1990's, can be used instead of an artificial anus for a patient who has undergone a surgical operation for rectal cancer. However, colorectal stents are not applicable to all patients who have undergone surgical operations for rectal cancer. Stent implantation is not a therapy for cancer, but a temporary treatment for preventing or counteracting disease-induced localized flow constriction, e.g., the narrowing of the intestine due to cancer. Typically, a colo-rectal stent is a tube made from metal wires, which is designed for insertion into a narrowed region of the large intestine and expansion thereat to counteract the flow constriction. For example, stents applicable to patients with colorectal cancer are commercially available in various types, and are most often made of a nickel and titanium alloy (commonly referred to as "Nitinol").

Recently, many attempts have been made to improve therapeutic effects with stents, i.e., stent implants capable of delivering drugs, such as thrombolytic agents or antihyperplasia agents. For example, U.S. Pat. No. 5,092,877 discloses self-expanding stents to which drug release coatings are applicable. Also, PCT Publication No. WO 1996/032907 describes a drug release coated stent.

In order to release a biologically active material over a long period, a method for coating a stent with a drug has been studied. Typically, the biologically active material is dissolved in a polymeric solvent and the solution is applied to a stent, followed by removing the solvent to afford a biologically active material-coated stent.

When a biologically active material, such as dexamethasone, is selected for use in application to stents, attention must be paid to miscibility and compatibility with the solvent or polymers used and to the release rate.

Korean Patent No. 10-439156 discloses a coating composition for drug release stents and a preparation method thereof, in which a coating composition comprising 0.01-30 wt % of a co-precipitation of a biologically active material selected from dexamethasone, paclitaxel and mitomycin with a water-soluble polymer and 70-99.99 wt % of a crosslinking polymer solvent is applied to a stent.

Korean Patent. No. 10-511618 discloses a multi-layer coating for drug release-controllable stents and a method for the preparation thereof. The multi-layer structure is composed of a base layer made of poly(ethylene-co-vinylacetate) or styrenic rubber polymer, a second coating layer made of a biocompatible polymer and a drug, and a third coating layer made of a different drug. Examples of the biocompatible polymer include polyvinylalcohol, polyethylene glycol, polylactide, polyglycolide, polylactide copolymer, polyethylene oxide, polydioxanone, polycaprolactone, polyphosphagen, polyanhydride, polyaminoacid, cellulose acetate butylate, cellulose triacetate, polyacrylate, polyacrylamide, polyurethane, polysiloxane, polyvinylpyrrolidone, and copolymers thereof. The drug used in the second layer may be selected from among anti-platelet agent containing cilostazol (6-[4-(1-cyclohexyl-1Htetrazol-5-yl)butoxy]-3,4-dihydro-2 (1H)-quinolinone, empirical formula $C_{20}H_{27}N_5O_2$, Mw 369.47), an anti-thrombolytic agent, an antihyperplasia agent, a growth factor, an antioxidant and a radio-active agent.

SUMMARY OF THE INVENTION

It is an object of the present invention to provide a release-controllable coating agent for drug releasing stents, a method for the preparation thereof, and a drug releasing stent coated therewith.

In accordance with an aspect thereof, the present invention provides a coating agent for drug releasing stents, comprising nanoparticles with a biologically active material entrapped therein, said particles being formed of a polyethyleneimine (PEI)-deoxycholic acid(DOCA) polymer (PDo) in which 1~8 moles of DOCA are grafted per mole of PEI.

In an embodiment, the biologically active material is taxol.

In accordance with another aspect thereof, the present invention provides a method for preparing a coating agent for drug releasing stents, comprising: (1) dissolving 1 mole of polyethyleneimine in 20 ml of dimethylformamide (DMF) to afford a first solution; (2) dissolving 1~8 moles of deoxycholic acid, along with a catalyst mixture consisting of 1.1~1.3 moles of DCC (dicyclohexyl carbodiimide) and 1.1~1.3 moles of HOSU (Hydroxy succinimide), in 20 ml of dimethylformamide to afford a second solution; (3) reacting the first solution with the second solution at room temperature for 12~24 hrs, with slow stirring, followed by filtration to give a filtrate; (4) dialyzing the filtrate through an 8,000 Å membrane to remove dimethylformamide and unreacted materials therefrom; (5) recovering a polyethyleneimine-deoxycholic acid polymer through dehydration; (6) dissolving 0.2 g of the polyethyleneimine-deoxycholic acid polymer and 0.01~0.03 g of a biologically active material in 4 ml of ethanol and removing ethanol from the solution through vacuum distillation; and (7) dispersing 0.5 ml of the resulting mixture in 1 ml of distilled water by vortexing and pipetting to produce nanoparticles.

In an embodiment, the method may further comprises mixing 4 ml of the mixture obtained in step (6) with 0.8 ml of distilled water and removing ethanol through vacuum distillation.

In another embodiment, the distilled water is deionized water.

In a further embodiment, each of the mixture and the distilled water is divided into 5~10 equal parts before removing ethanol.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
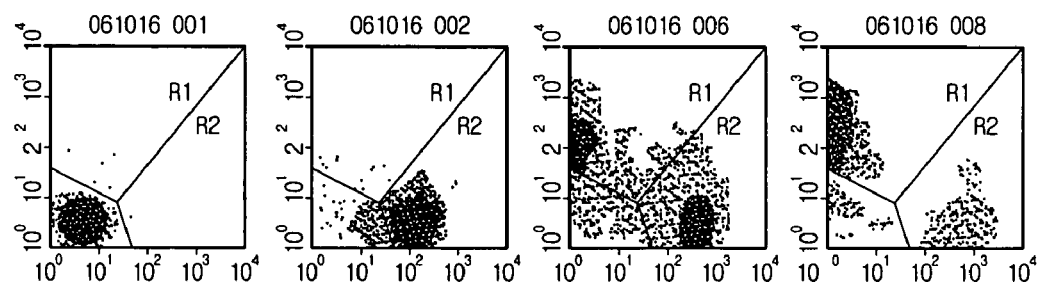
FIG. 1 shows assay results for cytotoxicity of coating agents for drug releasing stents according to the present invention.

Below, a detailed description will be given of the present invention with reference to the drawings.

In accordance with an aspect thereof, the present invention pertains to a coating agent for drug releasing stents. The coating agent according to the present invention is in the form of nanoparticles with a polyethyleneimine (PEI)-deoxycholic acid (DOCA) polymer (hereinafter referred to as "PDo") entrapped therein. The PDo has a PEI backbone to which deoxycholic acid (DOCA) is grafted in an amount of 1-8 moles per mole of PEI. PEI is represented by the following Chemical Formula 1.

The PEI useful in the present invention has a molecular weight ranging from 20,000 to 30,000 with an amine distribution of 25% for primary amine, 50% for secondary amine, and 25% for tertiary amine.

[Chemical Formula 2]

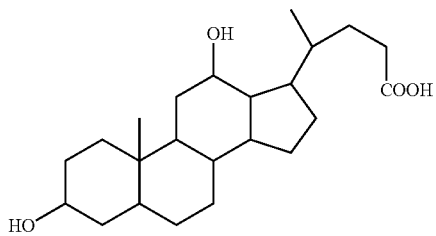

PDo is represented by the following Chemical Formula 3 and can be obtained through an amino bond (CONH) between

[Chemical Formula 1]

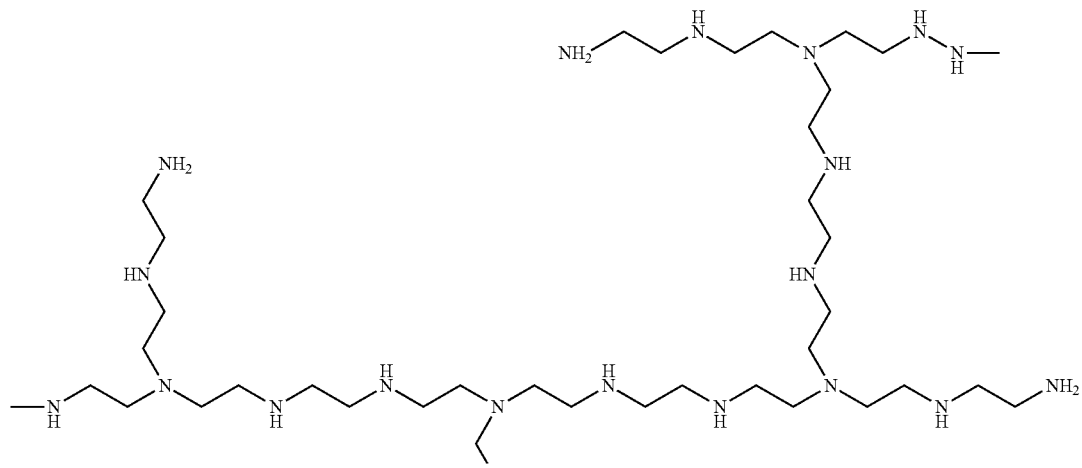

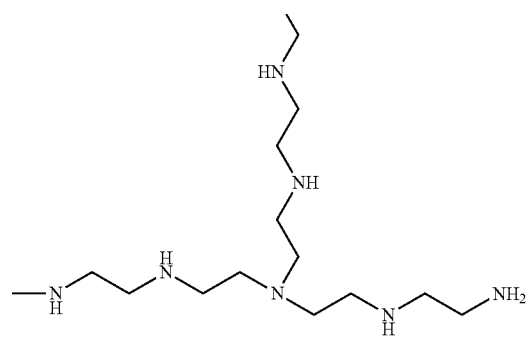

PEI: Polyethyleneimine the amino groups (—NH) of PEI and the carboxyl group (—COOH) of deoxycholic acid.

The distilled water useful in this step may be deionized water.

[Chemical Formula 3]

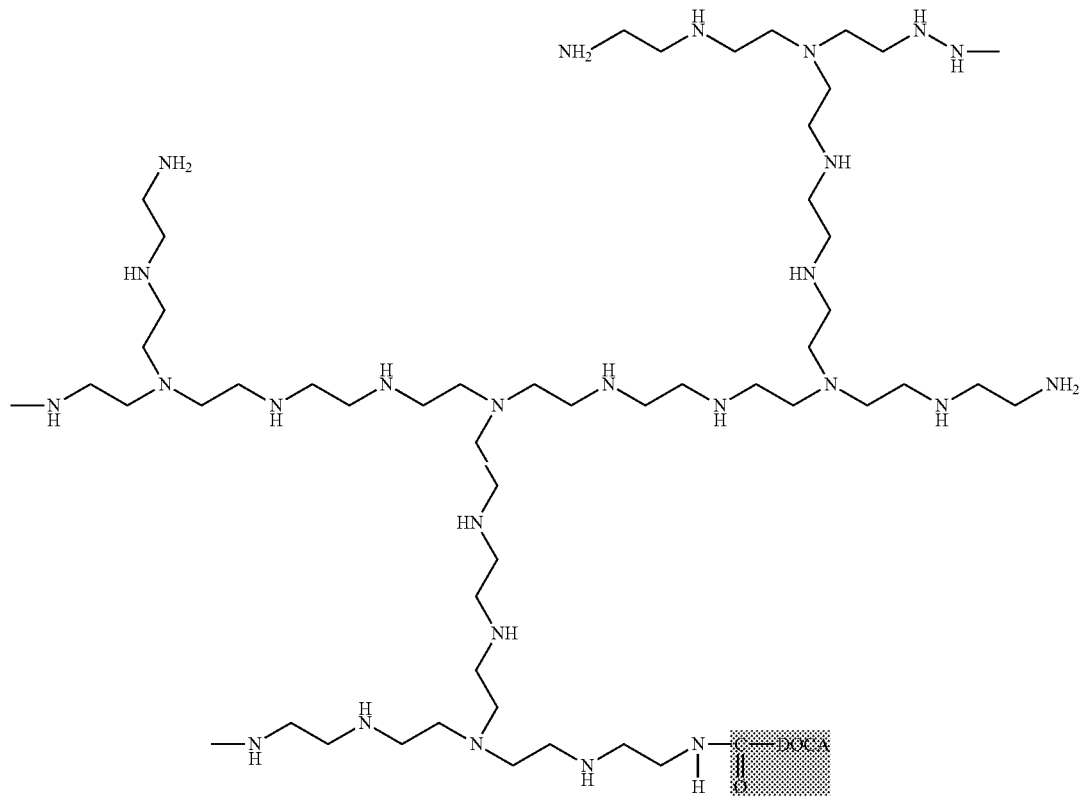

This polyethyleneimine-deoxycholic acid polymer can be molded into nanoparticles with a biologically active material entrapped therein and the nanoparticles are applied to the surface of the stent.

The biologically active material may be taxol.

In accordance with another aspect thereof, the present invention pertains to a method for preparing the coating composition for drug-releasing stents, comprising (1) dissolving 1 mole of polyethyleneimine in 20 ml of dimethylformamide (DMF) to afford a first solution; (2) dissolving 1~8 moles of deoxycholic acid, along with a catalyst mixture consisting of 1.1~1.3 moles of DCC (dicyclohexyl carbodiimide) and 1.1~1.3 moles of HOSU (Hydroxy succinimide), in 20 ml of dimethylformamide to afford a second solution; (3) reacting the first solution with the second solution at room temperature for 12~24 hrs, while slowly stirring and filtering the reaction; (4) dialyzing the filtrate through an 8,000 Å membrane to remove dimethylformamide and unreacted materials therefrom; (5) dehydrating the dialysate to recover a polyethyleneimine-deoxycholic acid polymer; (6) dissolving 0.2 g of the polyethyleneimine-deoxycholic acid polymer and 0.01~0.03 g of a biologically active material in 4 ml of ethanol and removing ethanol from the solution through distillation in vacuo; and (7) dispersing 0.5 ml of the resulting mixture in 1 ml of distilled water by vortexing and pipetting to produce nanoparticles.

In an embodiment, the method may further comprise mixing 4 ml of the mixture obtained in step (6) with 0.8 ml of distilled water and removing ethanol through vacuum distillation.

Before the ethanol is removed, the mixture and the distilled water may be divided into 5-10 equal parts.

A better understanding of the present invention may be grasped with reference to the following examples, which are set forth to illustrate, but are not to be construed to limit the present invention.

SYNTHESIS EXAMPLE 1

1 mole of deoxycholic acid (DOCA) was mixed with 1.2 moles of DCC and 1.2 moles of HOSU and dissolved in 20 ml of dimethylformamide. Separately, 1 mole of polyethyleneimine (PEI) was dissolved in 20 ml of dimethylformamide. After mixing the two solutions together, DOCA was allowed to react with PEI. Filtration was conducted to remove unnecessary factors. Through dialysis using an 8,000 Å membrane, the solvent dimethylformamide and unreacted materials were removed. After dialysis, the PEI-DOCA polymer thus synthesized (hereinafter referred to as "PDo1") was collected by freeze-drying the reaction product.

SYNTHESIS EXAMPLE 2

The same procedure as in Synthesis Example 1 was conducted, with the exception of using deoxycholic acid in an amount of 5 moles instead of 1 mole, to synthesize a PEI-DOCA polymer (hereinafter referred to as "PDo5").

SYNTHESIS EXAMPLE 3

The same procedure as in Synthesis Example 1 was conducted, with the exception of using deoxycholic acid in an amount of 8 moles instead of 1 mole, to synthesize a PEI-DOCA polymer (hereinafter referred to as "PDo8").

EXAMPLE 1

0.2 g of PDo1, PDo5 or PDo8, respectively prepared in Synthesis Examples 1 to 3, was dissolved, along with 0.02 g of taxol, in 4 ml of ethanol, followed by vacuum evaporation for about 20 min to remove the ethanol. The remainder was aliquoted into eppendorf tubes. 0.1 ml of tertiary distilled water was added to each tube, followed by completely removing ethanol in a high-speed vacuum evaporator for 30-40 min.

Afterwards, 1 ml of distilled water was added to each tube and the resulting residue was dispersed by vortexing and pipetting. The nanoparticles thus produced were collected in vials. The sample concentration was 100 g/l. Because taxol was hydrophobic, taxol could be entrapped within the nanoparticles by dissolving the nanoparticles, along with taxol, in ethanol, removing ethanol and dispersing the nanoparticles in water.

EXAMPLE 2

The three kinds of nanoparticles obtained in Example 1, that is, PDo5, PDo5, and PDo8 nanoparticles, were applied to the surface of commercially available stents.

EXPERIMENTAL EXAMPLE 1

The three kinds of nanoparticles obtained in Example 1, that is, PDo1, PDo5, and PDo8 nanoparticles, were analyzed for physical properties. The results are summarized in Table 1, below.

TABLE 1

| Samples 시료 | Size | | Surface Charge (Zeta Potential) | |
|---|---|---|---|---|
| | Taxol Present | Taxol Absent | Taxol Present | Taxol Absent |
| PDo1 | 360 | 197 | 3.95 | 2.95 |
| PDo5 | 183 | 120 | 10.97 | 7.84 |
| PDo8 | 437 | 156 | 7.65 | 4.82 |
| PEI | — | | 23.87 | |

EXPERIMENTAL EXAMPLE 2

PDo5, obtained in Example 1, was assayed for cytotoxicity. The results are depicted in FIG. 1.

As seen in the panels of FIG. 1 from the left to the right, respectively representing treatments with 0, 0.01, 0.3, and 0.5 g/l of PDo5, cell counts were observed to move from a live region (R2) to a dead region (R1).

EXPERIMENTAL EXAMPLE 3

Figure 2:
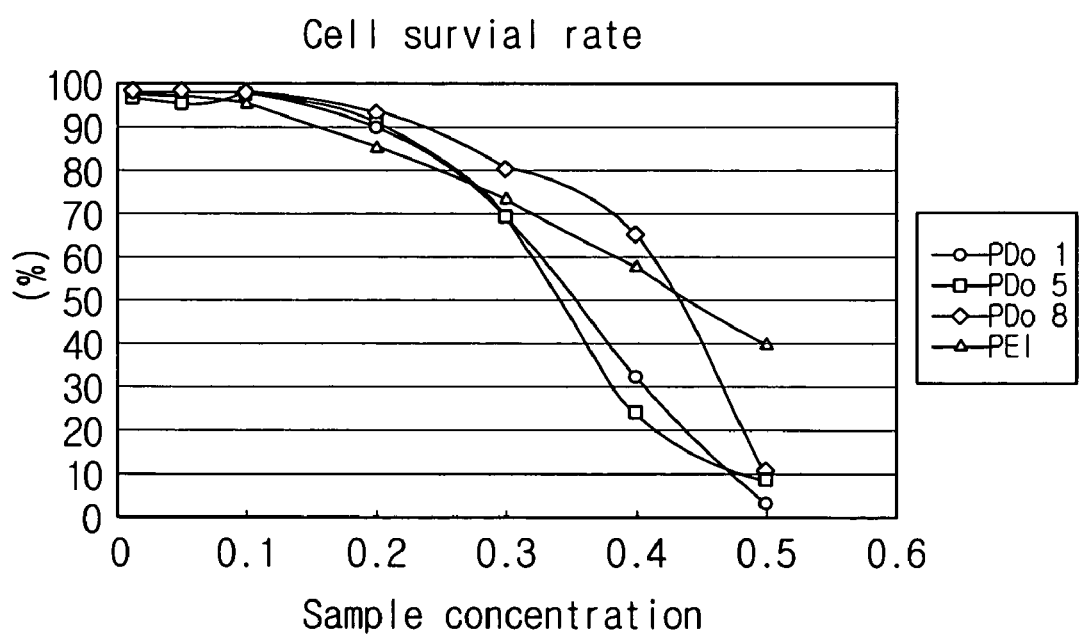
FIG. 2 is a graph showing cell survival rates of coating agents for drug releasing stents according to the present invention.

Using the PDo obtained in Example 1, cells were assayed for survival rate. The results are depicted in FIG. 2. As seen in FIG. 2, PDo8, which is higher in deoxycholic acid content than are the other PDos, was observed to ensure far higher cell survival rates than those of the other samples. Also, it was observed that the samples according to the present invention showed higher cell survival rates at an early stage than did polyethyleneimine alone, but sharply decreased in cell survival rate with increasing of sample concentration.

EXPERIMENTAL EXAMPLE 4

A polyurethane solution consisting of 2 wt % of polyurethane (Mw about 100,000) and 98 wt % of tetrahydrofuran was prepared. The three kinds of nanoparticles obtained in Example 1, that is, PDo1, PDo5, and PDo8 nanoparticles, were individually dissolved in ethanol. The polyurethane solution was mixed with the nanoparticle suspension and the resulting mixture was applied in two sets of five applications to the surface of commercially available Teflon-coated stents. As a result, the Teflon-coated stents were measured to be thickened from the Teflon thickness of 0.030 μm to 0.072 μm for a first test and to 0.075 μm for a second test.

On the basis of the amount of the coating agent consumed in the application, a load rate of taxol was calculated from the amount of taxol remaining in the coating agent. When calculating in consideration of the amount of the consumed coating agent and the amount of the initially loaded taxol, taxol was loaded in an amount of about 222 μg per unit area in the case of polyurethane.

EXPERIMENTAL EXAMPLE 5

Figure 3:
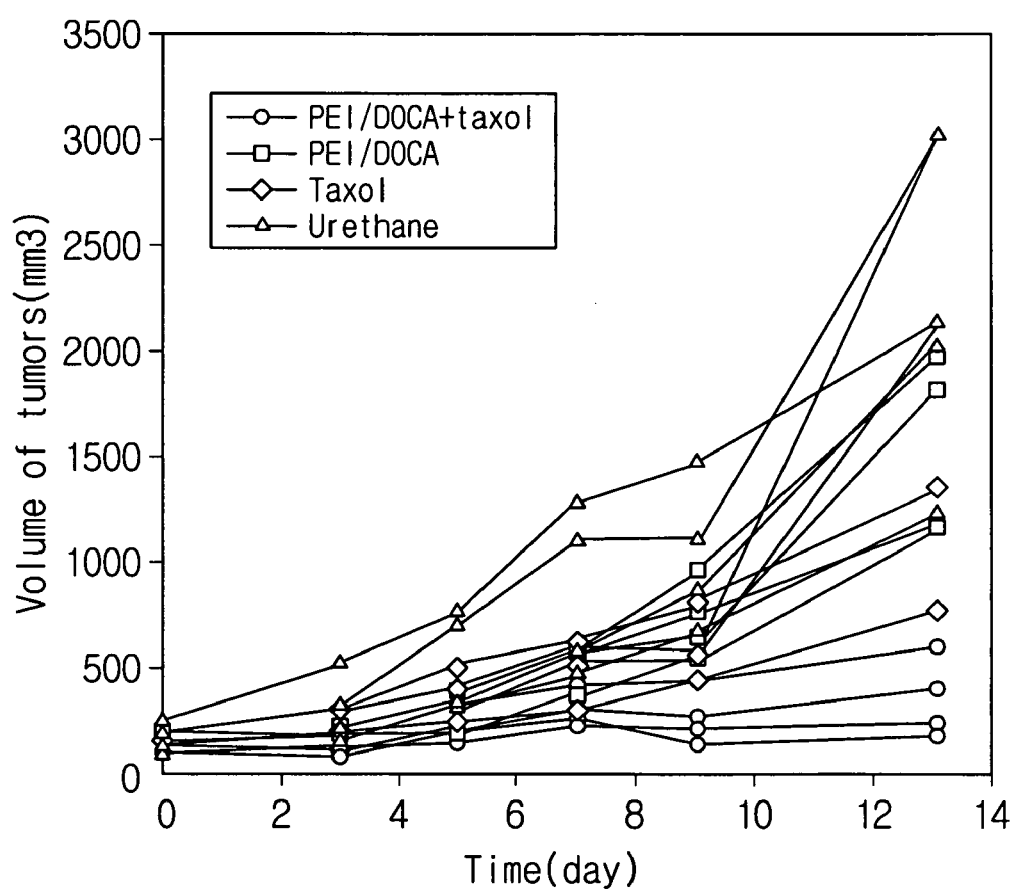
FIG. 3 is a graph in which cancer sizes are plotted against time upon treatment with coating agents for drug releasing stents according to the present invention.

Various dosage forms of coating agents, whether containing taxol or not, were assayed for anticancer activity in small animals (rats) by monitoring cancer sizes after the administration thereof, and the results are depicted in FIG. 3. Four experimental rats were allotted for each experiment group. Due to their toxicity to animals, the nanoparticles were used in a four-fold reduced amount when applied to the rats. In FIG. 3, polyurethane+polyethyleneimine/deoxycholic acid+taxol (PEI/DOCA+taxol) and polyurethane+taxol were used as a first and a second dosage form, respectively. In FIG. 3, in greater detail, the first dosage form (PEI/DOCA+taxol) refers to a coating agent prepared with polyurethane 600 mg+PEI/DOCA 20 mg+taxol 60 mg+tetrahydrofuran 7 ml, the second dosage form (PEI/DOCA) to a coating agent prepared with PEI/DOCA 20 mg+polyurethane 600 mg+tetrahydrofuran 7 ml, the third dosage form (taxol) to a coating agent prepared with polyurethane 600 mg+(PEI/DOCA 20 mg)+taxol 60 mg+tetrahydrofuran 7 ml, and the fourth dosage form to a coating agent prepared with polyurethane 600 mg+tetrahydrofuran 7 ml.

As seen in FIG. 3, the stent coated with polyurethane alone was observed to exhibit no anticancer activity in the experimental animals. The nanoparticles with taxol alone entrapped therein inhibited the growth of cancer cells in an early stage, but significantly decreased in anticancer activity over time. Particularly, death was observed in none of the experimental rats treated with the stents, indicating that the use of a suitable amount of the nanoparticles leads to the development of a material having a potent anticancer activity.

Thus, as is apparent from FIGS. 1 and 2, the polyethyleneimine used in the preparation of nanoparticles in accordance with the present invention plays an important role in introducing the biologically active material into cells and the nanoparticles show toxicity to cancer cells even when they contain no anticancer agents. Compared to a coating agent containing polyurethane only, the coating agent prepared with polyurethane and nanoparticles according the present invention shows no great difference in terms of drug release, but is regarded to exert greater anticancer effects on cells. Because they are larger in size than taxol molecules, the nanoparticles can keep the concentration of taxol high for a long period within the body. Taxol is apt to be rapidly discharged from the body as urine through the kidney due to the small molecular weight thereof. In addition, the nanoparticles of the present invention cannot enter normal cells, but can act on cancer cells, thus showing an EPR (enhanced permeation and retention) effect. Within the body, therefore, the nanoparticles of the present invention, covered with the polyurethane coat, are slowly exposed at cancer sites and release the entrapped taxol thereinto, thereby exerting anticancer activity specifically on cancer cells.

As described hereinbefore, a drug release-controllable coating agent is provided for drug releasing stents in accordance with the present invention. Also, a method for preparing the coating agent and a drug releasing stent coated with the coating agent are provided.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A coating agent for drug releasing stents, comprising a mixture of polyurethane and nanoparticles of a polyethyleneimine(PEI)-deoxycholic acid (DOCA) polymer (PDo), wherein a biologically active material is entrapped in said nanoparticles and wherein said polyethyleneimine(PEI)-deoxycholic acid (DOCA) polymer (PDo) is formed from 1-8 moles of DOCA per mole of PEI.

2. The coating agent according to claim 1, wherein the biologically active material is taxol.

* * * * *